United States Patent [19]

Bonin et al.

[11] Patent Number: 5,093,322
[45] Date of Patent: Mar. 3, 1992

[54] TICK-DERIVED AMBLYOMMIN AND METHOD OF ANTITHROMBIN THERAPY

[75] Inventors: Werner Bonin, Kelkheim; Paul Habermann; Dominique Tripier, both of Eppstein/Taunus; Elisabet Wöhner, Flörsheim am Main, all of Fed. Rep. of Germany

[73] Assignee: Hoechst Aktiengesellschaft, Frankfurt am Main, Fed. Rep. of Germany

[21] Appl. No.: 360,573

[22] Filed: Jun. 2, 1989

[30] Foreign Application Priority Data

Jun. 4, 1988 [DE] Fed. Rep. of Germany ....... 3819078

[51] Int. Cl.$^5$ ...................... C07K 15/00; A61K 37/64
[52] U.S. Cl. ........................................ 514/21; 530/350; 530/381; 530/855; 514/12
[58] Field of Search ...................... 530/350, 381, 855; 514/21, 12

[56] References Cited

U.S. PATENT DOCUMENTS 4,668,662  5/1987  Tripier .................. 514/12

OTHER PUBLICATIONS

P. Willadsen et al., Biochem. J., 189: 295–303, (1980).

J. Ribeiro et al., J. Exp. Med., vol. 161, pp. 332–344, (Feb. 1985).
K. Hellmann et al., Thrombosis Diath. Haemorrh., vol. 18, pp. 617–625, (1967).
Nieuwenhuizen & Gravesen, Biochimica Biophysica Acta, 668(1981) 81–88.

Primary Examiner—David L. Lacey
Assistant Examiner—Nina Ossanna
Attorney, Agent, or Firm—Finnegan, Henderson, Farabow, Garrett and Dunner

[57] ABSTRACT

The invention relates to a new active substance—amblyommin—for anticoagulant therapy and to a process for the isolation thereof from hard ticks. The isolated protein having a thrombin-inhibitory action has a molecular weight of 20000 to 30000 dalton, an isoelectric point between 5.05 and 5.65 and the partial amino acid sequences Ile-Leu-Phe-Thr-Gln-Gly-Asn-X-Gly-Glu-Leu-Glu-Asn-X-Phe-Glu-,
Lys-Ile-Leu-Phe-X-Gln-Gly- and
Ala-Ser-Tyr-Ile-Val-X-Ser-Glu-Ser-Ile-Gln-Ile-Leu-X-Leu-Ser-Glu-Gly-Ilein which each radical X can be identical or different and each represents a naturally occurring amino acid.

7 Claims, No Drawings

TICK-DERIVED AMBLYOMMIN AND METHOD OF ANTITHROMBIN THERAPY

The invention relates to the new active substance ambylommin for anticoagulant therapy, and to processes for the isolation thereof. Anticoagulants are of great importance for medicine. It is possible to mention as examples of problems central to medicine the prophylaxis of thrombosis, prophylaxis of arterial reocclusion, treatment of thromboses, consumption coagulopathy and the extracorporeal circulation. The agents customary in anticoagulant therapy at present often have some undesired disadvantages such as, for example, risk of hemorrhage, decrease in platelets, effect on the CNS, intolerance or indirect effect, as is observed, for example, with the heparin action scheme. Walsmann and Markwardt (Die Pharmazie vol. 36 (1981) page 653) describe the pharmaceutical importance of hirudin which is obtained from Hirudo medicinalis. This is a polypeptide which is 64–65 amino acids long (Chan, FEBS vol. 164 (1983) page 307; U.S. Pat. No. 4,668,662). The peptide is a highly specific thrombin inhibitor which appears to be otherwise pharmacologically inert. The disadvantages of the compound are the relatively short half-life of the compound and the parenteral administration form.

It is furthermore desirable to have a compound which has antithrombotic activity and has none of the disadvantages mentioned. It is therefore worthwhile to look for further anticoagulants which deal optimally with the above-mentioned medical problems.

Hard ticks of the family Ixodidae are in all stages of development temporary blood-sucking ectoparasites of reptiles, birds, mammals and humans. Adult female ticks usually remain several days on the host and suck up to one hundred times their own weight of blood. Ticks possess for this purpose piercing and sucking mouthparts composed of the chelicers, which are arranged in pairs, and the hypostome. The ticks use the cutting mechanism of the chelicers, the digits, to cut a wound in the epidermis, into which the chelicers themselves and the hypostome are inserted, thus forming the sucking channel. The salivary glands of most species of ticks produce a protein, called cement, which is discharged into the wound and into which the teeth of the hypostome become anchored and thus immobilize the ticks on the host in order to feed.

The ticks additionally discharge a secretion from their salivary glands which contains anticoagulants.

For blood sucking, the mouthparts of the ticks penetrate into the tissues, not directly into blood capillaries. They lyse tissue there, by means of the salivary gland enzymes, and damage very fine capillaries, from which blood emerges. Owing to the anticoagulant effect of the salivary gland secretion, the damaged vessels bleed for a while and thus produce a tissue vacuole, from which the ticks derive their food.

Thus, salivary glands of ticks have been investigated to obtain substances having anticoagulant properties.

The invention relates to a protein or a pharmaceutically acceptable salt thereof, which is isolated from hard ticks and inhibits blood coagulation via thrombin inactivation.

Although this protein and hirudin attack the same substrate, the two proteins are surprisingly distinctly different from one another. This suggests that the protein according to the invention—called amblyommin—will attain a medical importance different from that of hirudin. Amblyommin is a new protein. It is the first active substance isolated from the salivary glands of the southern African bont tick.

Amblyommin has the following physical properties. It has a relatively low affinity for ®Coomassie Brilliant Blue R250 Bio-Rad. After it has been freeze-dried it is only sparingly soluble in water. The protein is stable in all the buffers used. No reduction in activity is detectable after freezing of the eluate after HPLC purification at $-80°$ C. The compound is furthermore stable at $40°$ C. It can be precipitated with acetone at pH 1.8 (acetic acid or trichloroacetic acid). A solution of this precipitate is observed to have complete activity even after at least 12 days. When a Waters 600 multisolvent delivery system and a Biorad RP304 chromatography column are used for HPLC analysis, and a gradient from 80% A—20% B (with A=0.1% TFA and B=0.1% TFA in 80% acetonitrile in HPLC water) is applied, with 50% B being reached after a running time of 40 minutes. The retention time measured for amblyommin is 27 minutes. The protein is assigned a molecular weight of 20000–30000 dalton by gel filtration on G75 superfine material. A molecular weight of 26000 dt ±2000 dt is determined in a SDS polyacrylamide gel. Determination of the isoelectric point yields a value of about 5.35±0.3. Finally, the following partial amino acid sequences -Ile-Leu-Phe-Thr-Gln-Gly-Asn-X-Gly-Gln-Leu-Glu-Asn-X-Phe-Glu-, -Lys-Ile-Leu-Phe-X-Gln-Gly- and -Ala-Ser-Tyr-Ile-Val-X-Ser-Glu-Ser-Ile-Gln-Ile-Leu-X-Leu-Ser-Glu-Gly-Ile-have been identified, in which each radical X can be identical or different and each denotes a naturally occurring amino acid such as, for example, Tyr, Ser, Thr, Glu, Asp, Asn or any amino acid modified after translation, such as trimethyllysine or δ-carboxyglutamic acid.

The outstanding biological property is the specific inhibition of thrombin. The protein according to the invention is therefore used in medicine as an antithrombotic.

EXAMPLE 1

Isolation of the tick glands

The salivary gland of the ticks is a paired organ and is located in the sagittal direction on the right and left sides of the anterior half of the body. Depending on the functional state, the salivary gland is small in fasting specimens or extremely large in feeding ticks. The ticks used were members of the southern African bont tick Amblyomma hebraeum and Rhipicephalus evertsi, two colonies bred for years by known methods in the laboratory.

Partially fed females in the weight range 150–400 mg were taken from the host animal and immediately dissected under a stereomicroscope by fixing the ticks in a Petri dish with the back on double-sided adhesive tape and covered with PBS buffer, pH 7.2. After an incision with a fine scalpel along the periphery of the ticks, the upper and lower halves were opened out and the salivary glands were carefully removed and deep-frozen in nitrogen.

EXAMPLE 2

Extraction of the active substance from tick glands

Salivary glands from ticks of the genus Amblyomma hebraeum are isolated and then ground to a fine powder under nitrogen. The homogenate is dissolved in water and freeze-dried. The dried residue is vigorously shaken in 40% strength acetone at 40° C. for 30 minutes. The mixture is then centrifuged at 15000 g for 10 minutes. The sediment is again extracted as described, and the supernatant is combined with the first extraction, and 1 M acetic acid is slowly added until the pH has been adjusted to 5. The resulting precipitate is removed by centrifugation, and the clear supernatant is syphoned off. 10% strength trichloroacetic acid in acetone is added to the supernatant until a pH of 1.81 is reached. Then 10 times the volume of ice-cold acetone is added, and precipitation is carried out at −20° C. for 3.5 hours. The precipitate is removed by centrifugation in a Sorvall cooled centrifuge at 6000 rpm for 10 minutes. The sediment is washed with ice-cold acetone and ether and then resuspended in water. The suspension is frozen at −80° C. and then freeze-dried in a vacuum rotatory evaporator. The dried residue is taken up in buffer (0.05 M triethanolamine.HCl 0.4 M NaCl pH 7.8).

EXAMPLE 3

Gel filtration

The protein mixture prepared in Example 2 is purified by gel filtration. For this purpose, a column of diameter 1.6 cm and height 78.3 cm is packed with G 75 superfine material from Pharmacia. The flow rate is 10 ml/hour. The column has been calibrated with a gel filtration calibration kit from Pharmacia (Cat. No. 17-0442-01). Thrombin-inhibiting activity is found in fractions to which the molecular weight range 20000–30000 dt can be assigned.

EXAMPLE 4

Inhibition of coagulation of plasma

50 μl aliquots of the individual G 75 fractions are mixed with 50 μl of $H_2O$ and 100 μl of citrate-treated dog plasma which contained 3 U of thrombin per ml, and the thrombin time is determined. The procedure is that of Markwardt et al. (Pharmazie 43 (1988) 202; Fol. Haematol. 115 (1988) 70).

EXAMPLE 5

Inhibition of the thrombin-catalyzed cleavage of chromozyme TH

The determination is carried out as described in a publication by Griesbach et al. (Thromb. Res. 37 (1985), 347–50). This method is modified in such a way that the reaction is carried out in microtiter plate wells, with the final volume being 0.2 ml. The evaluation is carried out at 405 nm using an Elisa reader apparatus.

EXAMPLE 6

Purification by thrombin affinity column chromatography

Thrombin-Sepharose is prepared by the method of Walsmann, P. (Pharmazie 36 (1981) 860–861). The G 75 fractions which show activity are combined and freeze-dried, and the lyophilisate is taken up in 0.1 M acetic acid. Salts are removed from the samples on a cooled G 25 column, and the eluate is assayed for activity as in Example 5. Active fractions are combined and freeze-dried. The dried residue is taken up in 0.05 M Tris-HCl (pH 8) and loaded onto a prepared thrombin column. All the steps are carried out at 4° C. The column is washed twice with 0.05 M Tris buffer pH 8 before it is eluted with 5 M benzamidinium chloride in 0.05 M Tris-HCl (pH 8). The fractions are collected, and aliquots are removed, combined and dialyzed against $H_2O$ and assayed for thrombin inhibition. The fractions which show the highest activity are dialyzed and freeze dried. The lyophilisate is analyzed by SDS polyacrylamide gel electrophoresis with subsequent silver staining using a staining kit from Bio-Rad. A protein band is discovered in the MW range of about 25000 dt and is not observed on elution of the column without previous loading of the tick sample.

EXAMPLE 7

Growing the ticks

The three-host ticks of the species Rhipicephalus evertsi are grown as described by Th. Hiepe (Lehrbuch der Parasitologie (Parasitology Textbook) vol. 4, Gustav Fischer Verlag Stuttgart 1982, pages 46 et seq.). This takes about 3–4 months. Female ticks are stored at 28° C. and a humidity greater than 90% for egg-laying. After the larvae have hatched, the latter are placed on rabbits for the first blood meal. After the meal the molting to nymphs takes place fasting. The latter are placed on rabbits for the second blood meal. The replete nymphs now enter the differentiation stage to adult males and females. The adult animals are used after differentiation is complete.

EXAMPLE 8

Isolation of amblyommin from adult ticks

Adult ticks are homogenized in $H_2O$ in an Ultra-Turrax apparatus from Janke and Kunkel. The tick homogenate is then incubated at 40° C. for 40 minutes and then centrifuged in a Sorvall centrifuge at 10000 rpm and 5° C. for 30 minutes. The sediment is resuspended in $H_2O$ and again incubated at 40° C. for 30 minutes and then centrifuged. The supernatants from the two centrifugation steps are combined and filtered through blue ribbon filters. The clear supernatant is freeze-dried, and the residue is taken up in 20 mM Tris-HCl (pH 7.5) and then purified by Q-Sepharose fast flow chromatography (gradient 0–1 M NaCl in 20 mM Tris-HCl, pH 7.5). The amblyommin-containing fractions are identified as described in Example 5, freeze-dried and loaded onto a G 75 superfine column as in Example 3. The fractions with antithrombotic activity elute in the molecular weight range 20–30000 dt. They are combined and purified by reversed-phase HPLC on a Bio-Rad RP 304 column. The apparatus used is the Waters 600 multisolvent delivery system. The following gradient is run: start 80% A—20% B (with A=0.1% TFA and B=0.1% TFA in 80% acetonitrile) to 100% B in 60 minutes running time. The fractions with antithrombotic activity are combined, freeze-dried and again purified by reversed-phase HPLC. The following gradient is applied: start 80% A: 20% B (A=0.1% TF.A; B=0.1% TFA in 80% acetonitrile). 50% B is reached after a running time of 40 minutes. The retention time for the amblyommin fraction under these conditions is 27 minutes.

EXAMPLE 9

Determination of the molecular weight of amblyommin

The HPLC fraction of retention time 27 minutes is analyzed on a 17.5% SDS polyacrylamide gel. The electrophoresis calibration kit from Pharmacia (Cat. No. 17-0446-01) is used as molecular weight marker. In this system amblyommin migrates a short distance below carbonic anhydrase which is described as having a molecular weight of 30000 dt. The molecular weight of amblyommin emerges as 26000±2000 dt.

EXAMPLE 10

Determination of the isoelectric point

Amblyommin isolated as in Example 8 is subjected to ultra thin-layer focusing as suggested by Dr. Schulte et al. of LKB Instruments GmbH. The isoelectric point emerges as 5.35±0.3.

EXAMPLE 11

Amblyommin protein sequence analysis

We were unable to carry out N-terminal sequencing of authentic protein isolated from adult ticks. The available material was therefore subjected to trypsin cleavage. In order to allow quantitative trypsin cleavage, the protein is initially derivatized in a carboxymethylation reaction. For this purpose it is dissolved in 24 μl of buffer (8 M guanidinium.HCl, 10 mM Tris, 1 mM EDTA), and 51 μg of DTE in 4 μl of buffer and 4.52 μg of 2-mercaptoethanol in 5 μl are added. The reaction mixture is incubated at 37° C. for 1 hour and then 8.3 μl of an iodoacetamide solution (0.25 M iodoacetamide pH 8.0 adjusted with KOH) are added and the mixture is incubated at room temperature for 1 hour. Then 59 μl of $H_2O$ are added to dilute and, after addition of 400 μl of $C_2H_5OH$ and after vigorous shaking, precipitation and centrifugation at 12000 rpm are carried out. The sediment is then shaken with 100 μl of $CHCl_3$, and 300 μl of $H_2O$ are added and centrifugation is repeated. The upper phase is mixed with 300 μl of $C_2H_5OH$. The mixture is centrifuged and, for the trypsin cleavage, the sediment is dissolved in 66 μl of 0.2 M n-methylmorpholine (pH 8.5 adjusted with acetic acid). Then 5 μl of trypsin solution (3.3 μg of trypsin in N-methylmorpholine buffer) are added and the mixture is incubated at room temperature for 2 hours. The fragment mixture is now separated in a micro-bore reversed phase HPLC step. (Micro-bore column: 1 mm×25 cm, manufactured by Braun-Lee). For this purpose, a linear gradient from 10% A-60% B is applied (A=10% acetonitrile in HPLC water+0.1% TFA; B=10% $H_2O$ in acetonitrile+0.1% TFA). Three peak fractions can be readily isolated. They are dried individually on glass fiber filters in the gas-phase sequencer and subjected to sequence analysis. Used for this purpose is the 470 A gas-phase protein sequencer supplied by Applied Biosystems with online PTH identification system.

The following partial amino acid sequences were identified, with X representing the position occupied by a naturally occurring amino acid a) Ile-Leu-Phe-Thr-Gln-Gly-Asn-X-Gly-Gln-Leu-Glu-Asn-X-Phe-Glu b) Lys-Ile-Leu-Phe-X-Gln-Gly c) Ala-Ser-Tyr-Ile-Val-X-Ser-Glu-Ser-Ile-Gln-Ile-Leu-X-Leu-Ser-Glu-Gly-Ile.

We claim:

1. An isolated protein having a thrombin-inhibitory action or a pharmaceutically acceptable salt thereof, the protein being isolated from hard ticks and having a molecular weight of 20,000-30,000 daltons as determined by gel filtration, and an isoelectric point between 5.05 and 5.65.

2. An isolated protein or a pharmaceutically acceptable salt thereof as claimed in claim 1, said protein having the partial amino acid sequences
Ile-Leu-Phe-Thr-Gln-Gly-Asn-X-Gly-Gln-Leu-Glu-Asn-X-Phe-Glu-,
Lys-Ile-Leu-Phe-X-Gln-Gly-, and
Ala-Ser-Tyr-Ile-Val-X-Ser-Glu-Ser-Ile-Gln-Ile-Leu-X-Leu-Ser-Glu-Gly-Ile-
wherein X is an unknown amino acid.

3. An isolated protein or a pharmaceutically acceptable salt thereof, as claimed in claim 1, said protein having a molecular weight of 26000±2000 dalton.

4. An isolated protein or a pharmaceutically acceptable salt thereof, as claimed in claim 1, said protein having an isoelectric point of 5.35.

5. An isolated protein or a pharmaceutically acceptable salt thereof as claimed in claim 1, said protein being isolated from Rhipicephalus evertsi.

6. An isolated protein or a pharmaceutically acceptable salt thereof, as claimed in claim 1, said protein being isolated from Amblyomma hebraeum.

7. A method for the inhibition of thrombin, which comprises administering an effective amount of the protein or a physiologically tolerated salt of said protein as claimed in claim 1.

* * * * *